United States Patent [19]

Hoult

[11] Patent Number: 5,703,681
[45] Date of Patent: Dec. 30, 1997

[54] CARRIER AND ITS USE IN THE PREPARATION OF SAMPLES FOR SPECTROSCOPY

[75] Inventor: Robert A. Hoult, Beaconsfield, England

[73] Assignee: Perkin-Elmer LTD, Beaconsfield, England

[21] Appl. No.: 753,022

[22] Filed: Nov. 19, 1996

[30] Foreign Application Priority Data

Nov. 20, 1995 [EP]  European Pat. Off. ............. 95308277

[51] Int. Cl.$^6$ ................ G01N 1/04; G01N 1/28; G01N 21/35
[52] U.S. Cl. ........................ 356/36; 250/339.11
[58] Field of Search ............... 356/36, 38; 250/339.11, 250/339.12

[56] References Cited

U.S. PATENT DOCUMENTS

H901  3/1991  Eckart et al. .................. 250/304
5,326,972  7/1994  Codella ..................... 250/339.01

FOREIGN PATENT DOCUMENTS 2280133  1/1995  United Kingdom.

OTHER PUBLICATIONS

Applied Optics, 1 Aug. 1981, USA, vol. 20, No. 15, ISSN 0003-6935, pp. 2648-2655, XP002000561 Stuhlinger T W et al: "Bidirectional reflectance distribution function of gold-plated sandpaper" p. 2650.

Applied Spectroscopy, July-Aug. 1984, USA, vol. 38, No. 4, ISSN 0003-7028, pp. 604-605, XP002000562 Spragg R A: "A Rapid sample Preparation Technique For Diffuse Reflectance Measurements"-the whole document.

*Primary Examiner*—F. L. Evans
*Attorney, Agent, or Firm*—David Aker

[57] ABSTRACT

A carrier for use in preparing samples for spectroscopic analysis comprises a layer of abrasive material, e.g. sandpaper, created with a highly reflective material e.g. aluminium. The novel carrier reduces the effect of unwanted spectral components generated by the grit particle of the abrasive.

9 Claims, No Drawings

CARRIER AND ITS USE IN THE PREPARATION OF SAMPLES FOR SPECTROSCOPY

TECHNICAL FIELD

This invention relates to the preparation of samples for spectroscopy and in particular relates to the preparation of samples of solid materials.

BACKGROUND ART

In the field of mid-infrared spectroscopy of solids, a significant problem which has been encountered is the preparation of samples of the solid which are sufficiently thin to transmit significant amounts of infrared radiation in order to enable the spectroscopic analysis to take place. A known way of attempting to deal with the problem has been to abrade the solid material using a commercially available abrasive paper, e.g. sandpaper, which typically incorporates particles of SiO or $Al_2O_3$. This creates on or in the sandpaper small particles of the solid material to be investigated. The sandpaper is then placed in an instrument which can carry out the spectroscopic analysis and a spectrum of the sandpaper is measured in diffuse reflectance in a conventional way. This reveals the characteristic spectrum of the sample, in particular the small particles of the sample embedded in the sandpaper.

This technique has a number of drawbacks. Firstly, the loss of light inherent in the reflection from the grit particles of the sandpaper is substantial and this degrades the signal-to-noise ratio of the spectrum obtained. Secondly, the spectrum of the sandpaper contains features associated with the grit and/or with the binder used to secure the grit in place on the paper and these features interfere with the spectrum of the actual sample. In these prior art techniques it has often been necessary to obtain spectra from sandpaper, not containing the sample, in order to effectively eliminate the sandpaper spectrum. This is time consuming and inconvenient.

SUMMARY OF THE INVENTION

In the present invention we propose a technique which overcomes or alleviates these problems. According to the present invention there is provided a carrier for use in the preparation of samples for spectroscopic analysis, the carrier including a layer of abrasive material, said layer being coated with a relatively thin coating of highly reflective material. The abrasive material may be sandpaper. The coating may be a highly reflective metal such as aluminium. The thickness of the reflective coating will typically be in the range of 100 to 200 angstroms. This thickness is chosen to provide the necessary reflection, whilst at the same time enabling the abrasive properties of the abrasive material to remain essentially unchanged. The coating may be formed on the abrasive material by a conventional technique such as evaporative coating. It will be appreciated that the carrier can be supplied in various forms, e.g. an article of a form similar to a nail file.

DETAILED DESCRIPTION OF THE PREFERRED EMBODIMENT

In one example of the invention a carrier for use in the preparation of samples of hard polymer has been formed from sandpaper coated with a thin layer of aluminium, the thickness of that layer being in the range 100 to 200 angstroms. The aluminium was deposited on the surface of the sandpaper by evaporative coating. This carrier was then used to abrade a hard polymer material to form on the surface of the coated carrier, a sample of the polymer for spectroscopic analysis. The carrier was then placed in the spectroscopic instrument and reflective analysis using mid-infrared radiation carried out. The reflective coating of the sandpaper raises the general surface reflectivity by a substantial amount and at the same time prevents radiation from being absorbed by the underlying material, thus preventing the characteristic spectrum of the sandpaper from appearing in the reflection. The abrasive action of the sandpaper is substantially unaffected by the coating. The optical mechanism by which the spectrum of the sample is obtained probably changes from a diffuse scattering mixed with reflection-absorbtion to a more pure reflection-absorbtion mechanism.

It is envisaged that the grit size of the abrasive material may vary according to the solid material to be analysed. For example a softer material, such as chocolate, is likely to require a different grit size from that used with a hard polymer.

I claim:

1. A method of forming a sample of solid material for purposes of spectroscopic analysis, comprising the steps of:
   providing a carrier including a layer of an abrasive material, said layer being coated with a relatively thin coating of a highly reflective material; and
   abrading the solid material with the carrier to deposit a quantity of the solid material on the thin coating on the carrier.

2. A method according to claim 1 further comprising the step of subjecting the carrier, including the solid material, to spectroscopic analysis.

3. A method according to claim 1, wherein the abrasive material is sandpaper.

4. A method according to claim 1, wherein the coating is a highly reflective metal.

5. A method according to claim 4, wherein the metal is aluminum.

6. A method according to claim 1, wherein the thickness of the reflective coating is in the range of 100 to 200 angstroms.

7. The method according to claim 1, further comprising the step of forming the coating on the abrasive material by evaporative coating.

8. A method according to claim 2, wherein the abrasive material is sandpaper.

9. A method according to claim 2, wherein the coating is a highly reflective metal.

* * * * *